(12) United States Patent
Ortega

(10) Patent No.: US 7,114,257 B1
(45) Date of Patent: Oct. 3, 2006

(54) MULTI PURPOSE MACHINE

(76) Inventor: Hermis Ortega, 9001 SW. 122nd Ave., #307, Miami, FL (US) 33186

( * ) Notice: Subject to any disclaimer, the term of this patent is extended or adjusted under 35 U.S.C. 154(b) by 0 days.

(21) Appl. No.: 10/768,207

(22) Filed: Feb. 2, 2004

(51) Int. Cl.
 B26B 19/48 (2006.01)
 B26B 19/44 (2006.01)
 B26B 19/02 (2006.01)

(52) U.S. Cl. ............... 30/43.92; 30/34.05; 30/41.6; 30/133

(58) Field of Classification Search ............ 30/41.6, 30/43.92, 133, 196, 233, 200, 201, 34.05
See application file for complete search history.

(56) References Cited

U.S. PATENT DOCUMENTS

| | | | | |
|---|---|---|---|---|
| 2,183,442 A * | 12/1939 | Blackwell | | 30/41.5 |
| 2,716,279 A * | 8/1955 | Peterson | | 30/41.5 |
| 3,272,209 A * | 9/1966 | Kraus | | 132/213 |
| 3,343,259 A * | 9/1967 | Brodie | | 30/43.92 |
| 3,369,294 A * | 2/1968 | Shaw et al. | | 30/41.5 |
| 4,972,584 A * | 11/1990 | Baumann | | 30/133 |
| 5,084,973 A * | 2/1992 | Geer | | 30/133 |
| 5,261,161 A * | 11/1993 | Lee | | 30/41.5 |
| 6,378,210 B1* | 4/2002 | Bickford | | 30/43.92 |
| 2002/0108255 A1* | 8/2002 | Degregorio | | 30/133 |
| 2004/0006873 A1* | 1/2004 | Cutting | | 30/133 |

* cited by examiner

*Primary Examiner*—Hwei-Siu Payer
(74) *Attorney, Agent, or Firm*—Sanchelima & Accos., P.A.

(57) ABSTRACT

A portable multi purpose machine having removable head attachments primarily for personal grooming. The removable head attachments used for multiple purposes include: cutting and vacuuming, shaving, hair clipping, tooth brushing, vacuuming, and massaging. The multi purpose machine comprises a housing having first and second walls and a motor assembly. The motor assembly has an electrically powered drive member to operate each of the heads. A power cord assembly provides power to rechargeable batteries.

6 Claims, 7 Drawing Sheets

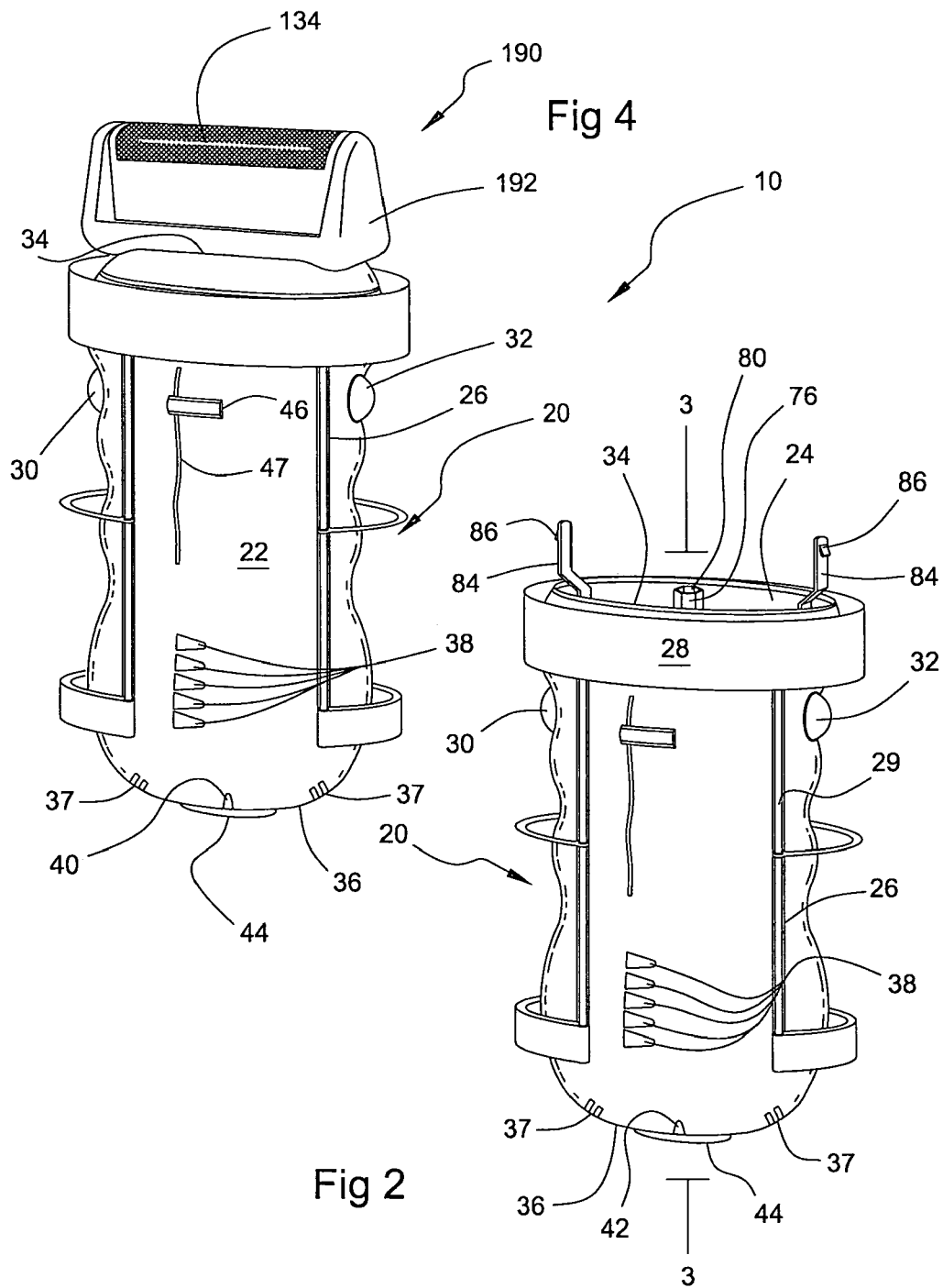

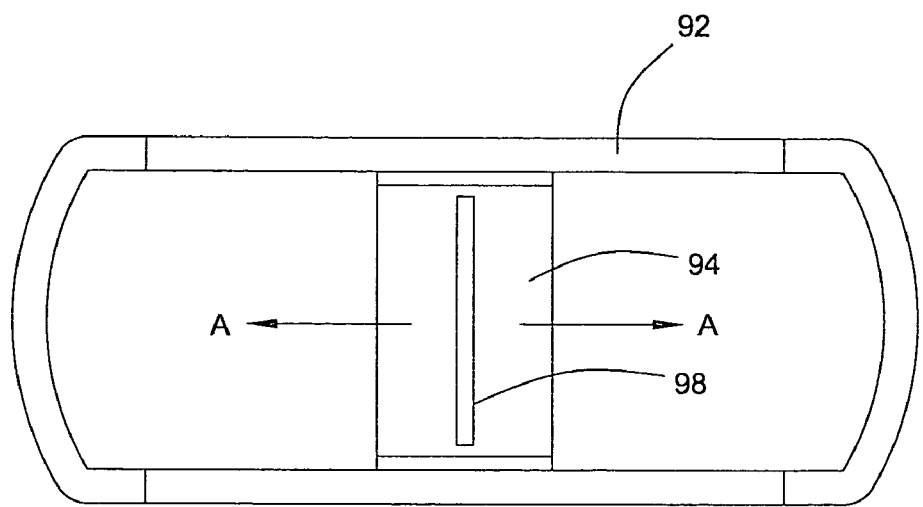
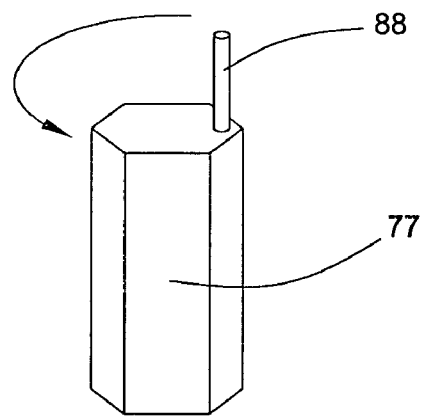
Fig 3a
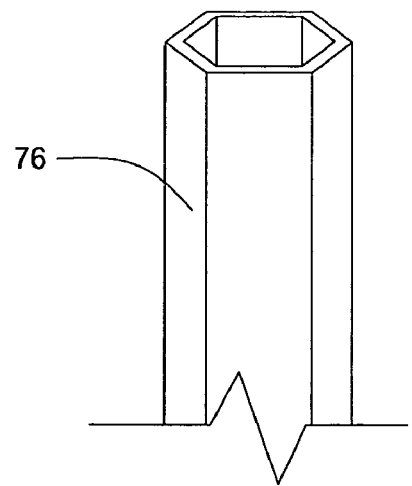

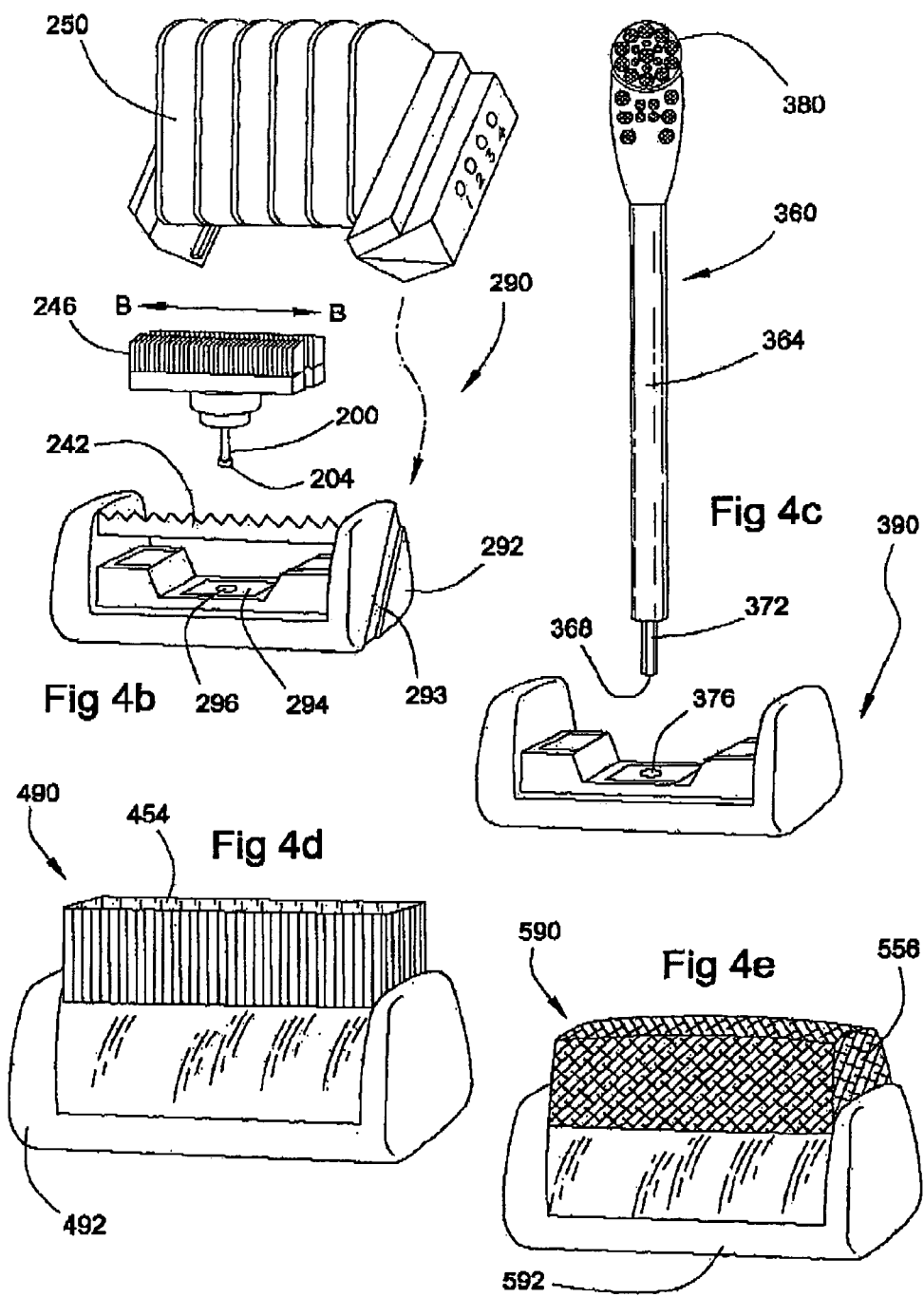

MULTI PURPOSE MACHINE

BACKGROUND OF THE INVENTION

1. Field of the Invention

The present invention relates to portable multi purpose machines, and more particularly, to a multi purpose machine having removable head attachments primarily for personal grooming.

2. Description of the Related Art

Many designs for grooming machines have been designed in the past. None of them, however, includes removable head attachments used for multiple purposes including: cutting, shaving, clipping, tooth brushing, vacuuming, and massaging.

There are no similar multi purpose machines to the best of applicant's knowledge, having removable head attachments, and are primarily for personal grooming.

SUMMARY OF THE INVENTION

A portable grooming machine, comprising a housing; a motor assembly and an electrically powered drive member mounted inside the housing; a power cord assembly removably connected to the housing; and a first head means removably secured upon the housing for cutting hair while vacuuming the hair into the housing. The first head means comprises a first cutter with a first coupling element that when assembled are housed within the first head means. The first coupling element transmits a first drive motion to the first cutter. The first coupling element is adapted to be set in a reciprocating motion by the electrically powered drive member and the first drive motion is transmitted to the first cutter.

The housing comprises first and second faces having a plurality of tracks. The plurality of tracks receives rails extending from a guard that extends above the first head means in an extended position and below the first head means in a retracted position.

Second head means are removably secured upon the housing for shaving hair. The second head means comprise a second cutter with a second coupling element that when assembled are housed within the second head means. The second coupling element transmits a second drive motion to the second cutter. The second coupling element is adapted to be set in the reciprocating motion by the electrically powered drive member and the second drive motion is transmitted to the second cutter.

A third head means is removably secured upon the housing for clipping hair. The third head means comprises a third cutter with a third coupling element that when assembled is housed within the third head means. The third coupling element transmits the second drive motion to the third cutter. The third coupling element is adapted to be set in the reciprocating motion by the electrically powered drive member and the second drive motion is transmitted to the third cutter.

A fourth head means is removably secured upon the housing for tooth brushing. The fourth head means comprises a circular tooth brush means having an engaging pin to the electrically powered drive member, transmitting either the first drive motion or the second drive motion.

A fifth head means is removably secured upon the housing for vacuuming. The fifth head means is substantially hollow to receive matter therethrough when the electrically powered drive member is engaged in the first drive motion.

A sixth head means is removably secured upon the housing for massaging. The sixth head means comprises a massage pad with a fourth coupling element. The fourth coupling element transmits either the first drive motion or the second drive motion to the massage pad. The fourth coupling element is adapted to be set in the reciprocating motion by the electrically powered drive member.

The housing has first and second switches, the first switch engaging the first drive motion and the second switch engaging the second drive motion. The housing also comprises a jack to receive the power cord assembly. In addition, the housing houses a rechargeable battery system, the rechargeable battery system recharged from the power cord assembly.

It is therefore one of the main objects of the present invention to provide a portable multi purpose machine having a plurality of removable heads.

It is another object of this invention to provide a portable multi purpose machine that is primarily used for personal grooming.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 2 shows a perspective view of the housing assembly.

FIG. 3a is a representation of an exploded view of the head assembly underside, male adaptor, and female shaft.

FIG. 4 represents a perspective view of the instant invention with a dry shaver head assembly.

FIG. 4b is a representation of an exploded view of a hair clipper head assembly.

FIG. 4c is a representation of an exploded view of a toothbrush head assembly.

FIG. 4d is a representation of a vacuum head assembly.

FIG. 4e is a representation of a massage head assembly.

DETAILED DESCRIPTION OF THE PREFERRED EMBODIMENT

Figure 1:
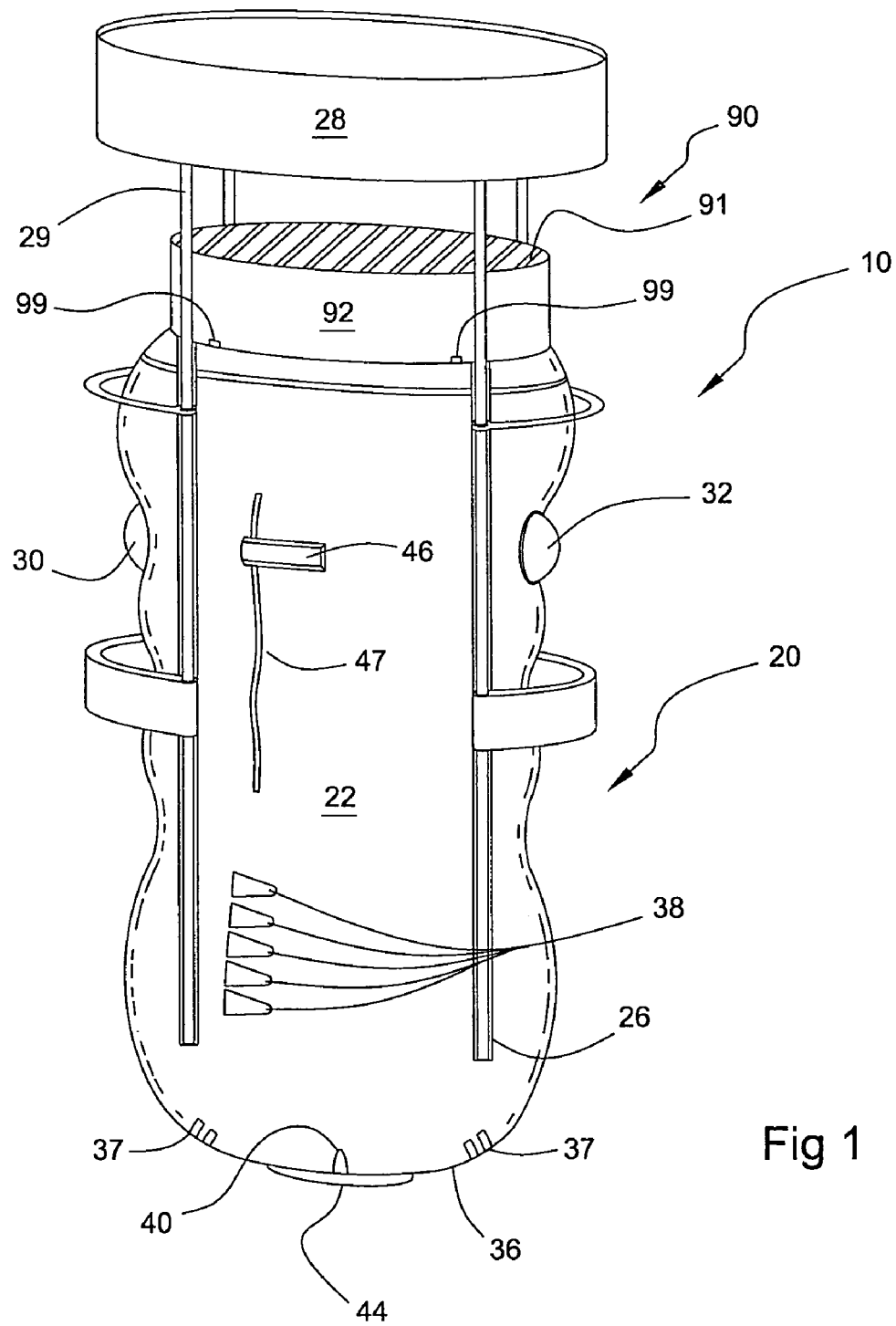
FIG. 1 represents a perspective view of the instant invention.

Referring now to the drawings, where the present invention is generally referred to with numeral 10, it can be observed that it basically includes housing 20, motor assembly 70, head assembly 90, and power supply cord assembly 600.

As seen in FIG. 1, seated on housing 20 is a hair-cutting/vacuum head assembly 90 having detachably secured head 92. Instant invention 10 comprises housing 20 having face 22 on its front side and face 24 on its rear side, seen in FIG. 3. Arranged on each side where faces 22 and 24 meet, are switch 30 and vacuum switch 32. Provided at end 36 where faces 22 and 24 also meet is socket 44 for connection to power supply cord assembly 600, seen in FIG. 5. Housing 20 has indicator lights 38 and 40. Indicator lights 38 indicate the amount of battery power remaining for instant invention 10 to operate. When all of indicator lights 38 are lit, it indicates full battery charge in battery 52, seen in FIG. 3, and when none of indicator lights 38 are lit, it indicates no battery charge remaining in battery 52. Indicator light 40 illuminates when power supply cord assembly 600 is connected and supplying electrical power to charge/recharge battery 52. Also seen on housing 20 is speed control lever 46 that rides within channel 47. Speed control lever 46 controls the speed at which motor assembly 70 is operating. Guard 28 has rails 29, which slide upon tracks 26. A user may adjust guard 28 to a predetermined height when cutting hair, wherein hair to be cut is placed through the mid section of guard 28 and is cut by head 92. The user may cut hair utilizing head 92 while vacuuming the hair simultaneously when activating instant invention 10 with vacuum switch 32.

Figure 1A:
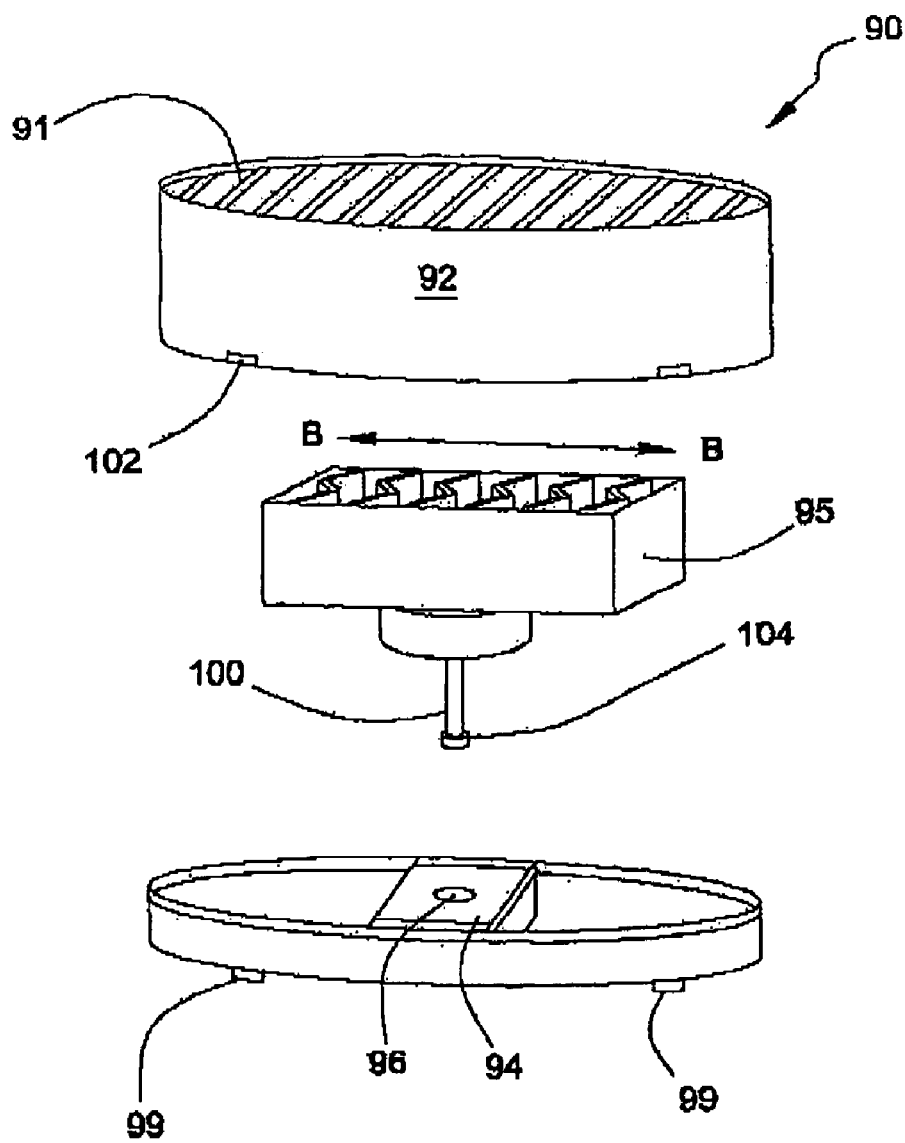
FIG. 1a is a representation of an exploded view of a hair-cutting/vacuum head assembly.

FIG. 1a shows an exploded view of the removable head assembly 90 in which a hair-cutting/vacuum unit comprises an under cutter 95 with a coupling element 94, which when assembled, is housed within head 92. Coupling element 94 transmits the drive motion to under cutter 95. Coupling element 94, which is adapted to be set in a reciprocating motion by the electric drive mechanism from motor 70, is coupled via drive pin 88 mounted upon male adaptor 77, as seen in FIG. 3a. Hair that is placed upon cutting foil 91 is cut by under cutter 95 and falls through either side of coupling element 94 as it is vacuumed. Coupling element 94 has aperture 96 for insertion of pin 100 having notch 104. Tabs 99 align with and engage into holes 102 when head 92 is assembled.

As seen in FIG. 2, housing 20 has head bracket arms 84. Bracket arms 84 have tabs 86 upon which all head assemblies removably snap thereon. While switch 30 is in the "on" position, female shaft 76 spins in a clockwise direction. While switch 32 is in the "on" position, female shaft 76 spins in a counter-clockwise direction.

Figure 3:
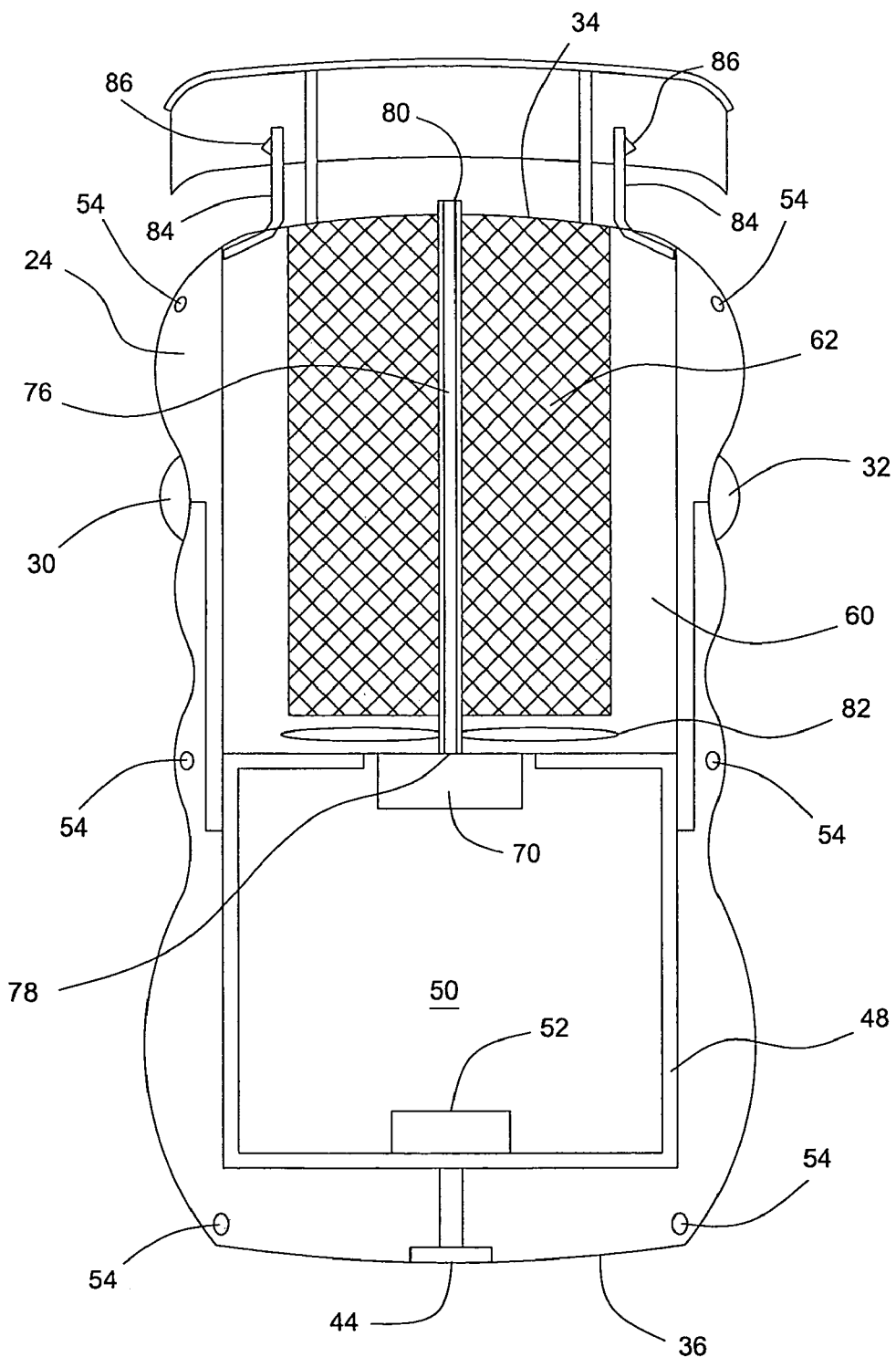
FIG. 3 illustrates a cut view of the housing assembly taken along the line 3—3 as seen in FIG. 2.

As seen in FIG. 3, face 24 of housing 20 comprises electrical cavity 48 and collector cavity 60. Instant invention 10 is powered by battery 52, which is positioned in electrical system 50. Electrical wires from shaver socket 44 connect to battery 52 for charging and recharging. Also within electrical system 50 is motor assembly 70. Electrical wires from switch 30 and vacuum switch 32 send electronic signals to engage motor 70. Extending from motor 70 and through collector 62 is female shaft 76. Female shaft 76 has shaft ends 78 and 80 and in the preferred embodiment, is an allen-type shape shaft.

Extending approximately perpendicularly from female shaft 76 and below collector 62 is propeller 82. While switch 30 is in the "on" position, female shaft 76 spins in a clockwise direction, causing propeller 82 to spin in a clockwise direction and direct air flow from vents 37, seen in FIG. 1, through electrical cavity 48, collector cavity 60, and out through head assembly 90. This airflow cools instant invention 10.

While switch 32 is in the "on" position, female shaft 76 spins in a counter-clockwise direction, causing propeller 82 to spin in a counter-clockwise direction and direct air flow from head assembly 90 at end 34, through collector cavity 60, electrical cavity 48, and out through vents 37, seen in FIG. 1. Collector 62, within collector cavity 60, collects hair, particles, and matter in general when instant invention 10 is utilized in a vacuum manner, such as with heads 92 and 492, seen in FIGS. 1 and 4d respectfully.

Face 24 comprises a plurality of apertures 54. Pins, not seen, extending from face 22, align with and snap into apertures 54 when housing 20 is assembled.

Seen in FIG. 3a are female shaft 76, male adaptor 77, and a bottom view of head 92. In operation, drive pin 88 makes engagement with groove 98 of coupling element 94, causing back-and-forth movement in the directions of arrow A for transmission of a drive motion reciprocating in the directions of arrow B to under cutter 130, seen in FIG. 4a, mounted for oscillatory motion in head 192. Similarly, in operation, drive pin 88 makes engagement with groove 98 of coupling element 94, causing back-and-forth movement in the directions of arrow A for transmission of a drive motion reciprocating in the directions of arrow B to under cutter 95, seen in FIG. 1a, mounted for oscillatory motion in head 92.

Figure 4A:
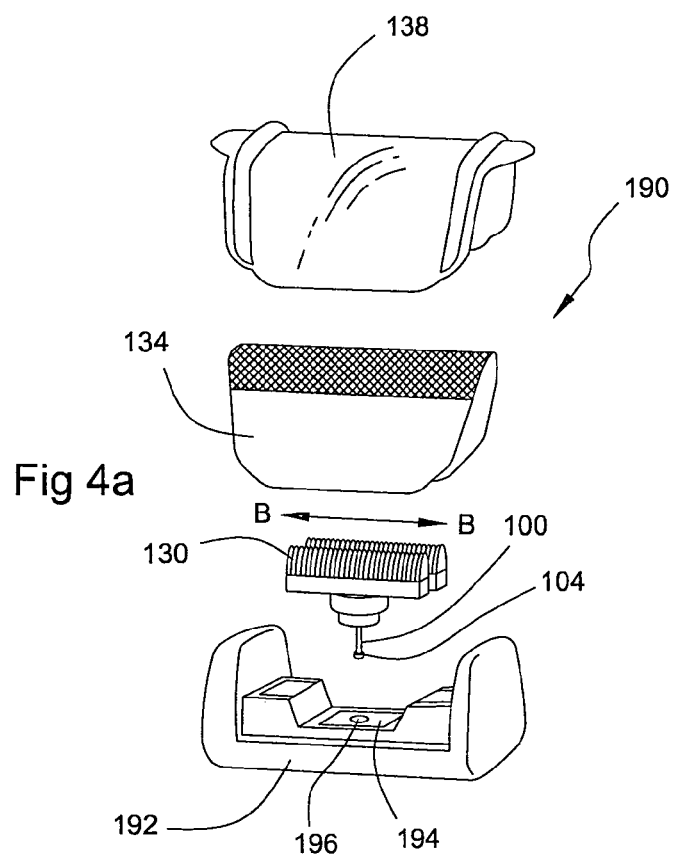
FIG. 4a is a representation of an exploded view of a dry shaver head assembly.

Seen in FIGS. 4 and 4a is a shaving head assembly 190 having detachably secured head 192. Removable head assembly 190 as a hair-shaving unit comprises an under cutter 130 with a coupling element 194, which when assembled, is housed within shaver foil 134. Coupling element 194 transmits the drive motion to under cutter 130. Coupling element 194, which is adapted to be set in a reciprocating motion by the electric drive mechanism from motor 70, is coupled via drive pin 88 mounted upon male adaptor 77. Coupling element 194 has aperture 196 for insertion of pin 100 having notch 104. Foil protector cap 138 protects shaver foil 134 when not in use.

FIG. 4b shows an exploded view of removable head assembly 290 in which a hair-clipping unit comprises head 292 having a clipper plate 242. Biased against clipper plate 242 is a clipper 246. As with removable head assembly 190, coupling element 294 transmits the drive motion to clipper 246. The coupling element 294, which is adapted to be set in a reciprocating motion by the electric drive mechanism from motor 70, is coupled via drive pin 88 mounted upon male adaptor 77.

Similarly as when used in the hair-shaving defined above, in operation of removable head assembly 290, drive pin 88 makes engagement with groove 98, seen in FIG. 3a, of coupling element 294, causing back-and-forth movement in the directions of arrow A for transmission of a drive motion reciprocating in the directions of arrow B to clipper 246, causing hair to be clipped and/or cut when biased against clipper plate 242. Guard 250 slides within track 293 to adjust the length of hair to be clipped and/or cut. The numbers on the side of guard 250 represent the length of hair to be clipped and/or cut. Coupling element 194 has aperture 196 for insertion of pin 200 having notch 204.

FIG. 4c shows a perspective view of the removable head assembly 390 having toothbrush assembly 360. Toothbrush assembly 360 comprises circular toothbrush 380 mounted upon handle 364. Extending from handle 364 and in opposite direction from circular toothbrush 380, is male shaft 372 terminating at end 368. Removable head assembly 390 has through-hole 376. When assembled for operation, male shaft 372 is inserted through through-hole 376 and directly into female shaft 76. Circular toothbrush 380 may be operated with either switch 30 or vacuum switch 32. In operation, male shaft 372 extends through handle 364 to drive circular toothbrush 380.

FIG. 4d shows a perspective view of the removable head assembly 490 in which a vacuum unit comprises head 492 having a brush 454. When vacuum switch 32 is in the "on"

position, female shaft 76 spins in a counter-clockwise direction, causing propeller 82 to spin in a counter-clockwise direction, thus creating a vacuum. Head 492 is mostly hollow to allow matter to pass into collector 62.

FIG. 4e shows a perspective view of removable head assembly 590 comprising head 592 and massage pad 556. As with removable head assemblies 190 and 290, coupling element 194, seen in FIG. 4a, transmits the drive motion to massage pad 556. The coupling element 194, which is adapted to be set in a reciprocating motion by the electric drive mechanism from motor 70, is coupled via drive pin 88 mounted upon male adaptor 77.

Similarly as when used in the hair-shaving and hair-clipping defined above, in operation of removable head assembly 590, drive pin 88 makes engagement with groove 98, seen in FIG. 3a, of coupling element 194, causing back-and-forth movement in the directions of arrow A for transmission of vibration, causing massage pad 556 to vibrate.

Figure 5:
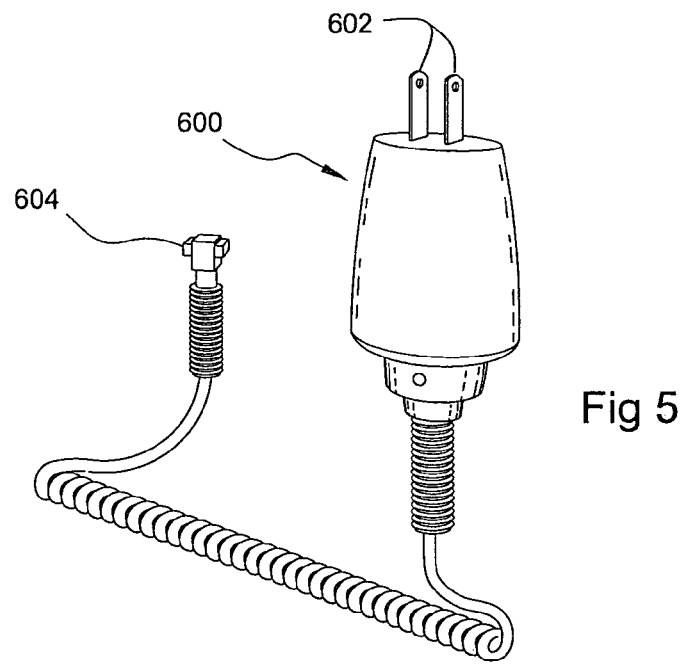
FIG. 5 shows a perspective view of the power supply cord assembly.

As seen in FIG. 5, power supply cord assembly 600 comprises plug blades 602, which are inserted into an electrical outlet for power and power plug 604, which is inserted into shaver socket 44. Electrical wires from shaver socket 44 connect to battery 52 for charging and recharging, as seen in FIG. 3.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A portable grooming machine kit, comprising
   a) a housing comprising first and second faces having A plurality of tracks, said plurality of tracks receiving rails extending from a guard that extends a first predetermined distance in an extended position and a second predetermined distance in a retractable position;
   b) a motor assembly and an electrically powered drive member mounted inside said housing;
   c) a power cord assembly removably connected to said housing;
   d) a first head means removably secured upon said housing for cutting hair while vacuuming said hair into said housing, said first head means comprising a first cutter with a first coupling element that when assembled are housed within said first head means, said first coupling element transmits a first drive motion to said first cutter, said first coupling element is adapted to be set in a reciprocating motion by said electrically powered drive member and said first drive motion is transmitted to said first cutter;
   e) a second head means removably secured upon said housing for shaving hair, said second head means comprising a second cutter with a second coupling element that when assembled are housed within said second head means, said second coupling element transmits a second drive motion to said second cutter, said second coupling element is adapted to be set in said reciprocating motion by said electrically powered drive member and said second drive motion is transmitted to said second cutter;
   f) a third head means removably secured upon said housing for clipping hair, said third head means comprising a third cutter with a third coupling element that when assembled is housed within said third head means, said third coupling element transmits said second drive motion to said third cutter, said third coupling element is adapted to be set in said reciprocating motion by said electrically powered drive member and said second drive motion is transmitted to said third cutter; and
   g) a fourth head means removably secured upon said housing for tooth brushing, said fourth head means comprising a circular tooth brush means having an engaging pin to said electrically powered drive member transmitting either said first drive motion or said second drive motion.

2. The portable grooming machine kit forth in claim 1, further comprising a fifth head means removably secured upon said housing for vacuuming, said fifth head means being substantially hollow to receive matter therethrough when said electrically powered drive member is engaged in said first drive motion.

3. The portable grooming machine kit forth in claim 2, further comprising a sixth head means removably secured upon said housing for massaging, said sixth head means comprising a massage pad with a fourth coupling element, said fourth coupling element transmits either said first drive motion or said second drive motion to said massage pad, said fourth coupling element is adapted to be set in said reciprocating motion by said electrically powered drive member.

4. The portable grooming machine kit forth in claim 3, further characterized in that said housing has first and second switches, said first switch engaging said first coupling element and said second switch engaging said second coupling element.

5. The portable grooming machine kit forth in claim 4, further characterized in that said housing comprises a jack to receive said power cord assembly.

6. The portable grooming machine kit forth in claim 5, further characterized in that said housing houses a rechargeable battery system, said rechargeable battery system recharged from said power cord assembly.

* * * * *